United States Patent [19]
Taylor et al.

[11] Patent Number: 5,830,434
[45] Date of Patent: Nov. 3, 1998

[54] METHODS OF TREATING NON-INSULIN DEPENDENT DIABETES MELLITUS WITH PANCREATIC POLYPEPTIDE

[75] Inventors: Ian L Taylor, Kiawah Island; Thomas Gettys, Mt. Pleasant, both of S.C.

[73] Assignee: Medical University of South Carolina Foundation for Research Development, Charleston, S.C.

[21] Appl. No.: 806,203

[22] Filed: Feb. 26, 1997

[51] Int. Cl.[6] ........................... A61K 49/00; A61K 38/28; A61K 38/08

[52] U.S. Cl. ................................... 424/9.2; 514/2; 514/4; 514/12; 514/17; 514/866; 435/810; 530/303; 530/324; 530/329

[58] Field of Search .................................. 424/9.2; 514/2, 514/4, 17, 12, 866; 530/303, 300, 324, 329; 435/810, 7.21

[56] References Cited

PUBLICATIONS

Hermann, LS et al. Diabetes Care. 17(10): 1100–1109, Oct. 1994.

Michael W. Schwartz et al., "Specificity of Leptin Action on Elevated Blood Glucose Levels and Hypothalamic Neuropeptide Y Gene Expression in ob/ob Mice", *Diabetes*, 45:531–535, Apr. 1996.

Robert V. Considine et al., "Serum Immunoreactive–Leptin Concentrations in Normal–Weight and Obese Humans", *The New England Journal of Medicine*, 334(5):292–295, Feb. 1, 1996.

Isabelle Cusin et al., "The ob Gene and Insulin", *Diabetes*, 441:1467–1469.

Davis S. Weigle et al., "Recombinant ob Protein Reduces Feeding and Body Weight in the ob/ob Mouse", *J. Clin. Invest.*, 96:2065–2070, Oct. 1995.

Toshikatsu Okumura et al., "Pancreatic Polypeptide Microinjection Into the Dorsal Motor Nucleus Inhibits Pancreatic Secretion in Rats", *Gastroenterology*, 108:1517–1525, 1995.

Takayoshi Kiba et al., "Ventromedial Hypothalamic Lesion–Induced Vagal Hyperactivity Stimulates Rat Pancreatic Cell Proliferation", *Gastroenterology*, 110:885–893, 1996.

Neal E. Seymour et al., "Altered Hepatocyte Insulin Binding in Chronic Pancreatitis", *Digestive Diseases and Sciences*, 39(8):1740(46), Aug. 1994.

D.K. Anderson et al., "Rapid Hormone–Induced Changes in Hepatic Insulin (INS) Binding are Impaired in Chronic Pancreatitis (CP)", *Degestive Diseases and Sciences*, 39(8):1741(48).

Gary G. Berntson et al., "Pancreatic Polypeptide Infusions Reduce Food Intake in Prader–Willi Syndrome", *Peptides*, 14:497–503, 1993.

Tom W. Gettys et al., "Insulin–Sparing Effects of Pancreatic Polypeptide in Congenitally Obese Rodents", *Pancreas*, 6(1):46–53, 1991.

D.C. Whitcomb et al., "Characterization of Saturable Binding Sites for Circulating Pancreatic Polypeptide in Rat Brain", *American Journal Physiology*, 259–:G687–G691.

You Su Sun et al., Reversal of Abnormal Glucose Metabolism in Chronic Pancreatitis by Administration of Pancreatic Polypeptide, *The American Journal of Surgery*, 151:130–140, Jan. 1986.

R.J. Gates and N.R. Lazarus, "The Ability of Pancreatic Polypeptides (APP and BPP) to Return to Normal the Hyperglycaemia, Hyperinsulinaemia and Weight Gain of New Zealand Obese Mice", *Hormone Research*, 8:189–202, 1977.

F. Rohner–Jeanrenaud and B. Jeanrenaud, "Obesity, Leptin, and the Brain", *The New England Journal of Medicine*, 334(5):324–325, Feb. 1, 1996.

*Primary Examiner*—David Saunders
*Assistant Examiner*—F. Pierre VanderVegt
*Attorney, Agent, or Firm*—Needle & Rosenberg, P.C.

[57] ABSTRACT

The present invention provides a method of treating NIDDM in a patient diagnosed with NIDDM by administering to the patient a compound in a pharmaceutically acceptable carrier that reduces hepatic glucose production in the patient by inhibiting hepatic expression of the alpha subunit of a $G_s$ protein in a liver cell plasma membrane, thereby inhibiting stimulation of cAMP by glucagon, whereby the reduction in hepatic glucose production treats the NIDDM. Also provided is a method for screening compounds for the ability to treat NIDDM comprising determining if the compound decreases hepatic expression of the alpha subunit of a $G_s$ protein in a liver cell plasma membrane, thereby inhibiting the stimulation of cAMP by glucagon, a compound which decreases the hepatic expression of the alpha subunit of the $G_s$ protein in the liver cell plasma membrane, thereby inhibiting the stimulation of cAMP by glucagon, being a compound with the ability to treat NIDDM. The present invention further provides a kit for treating NIDDM comprising a compound in a pharmaceutically acceptable carrier that decreases hepatic expression of the alpha subunit of the $G_s$ protein in the liver cell plasma membrane, thereby inhibiting stimulation of cAMP by glucagon.

26 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 36 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:1:

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

( 2 ) INFORMATION FOR SEQ ID NO:2:

( i ) SEQUENCE CHARACTERISTICS:
( A ) LENGTH: 6 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:2:

Leu Thr Arg Pro Arg Tyr
1               5

( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:3:

```
Leu  Thr  Arg  Pro  Arg  Tyr
1                   5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:4:

```
Leu  Thr  Arg  Pro  Arg  Tyr
1                   5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:5:

```
Leu  Thr  Arg  Pro  Arg  Tyr
1                   5
```

METHODS OF TREATING NON-INSULIN DEPENDENT DIABETES MELLITUS WITH PANCREATIC POLYPEPTIDE

This invention was made with government support under grant no. DK 40772 awarded by the National Institutes of Health. The government has certain rights in the invention.

BACKGROUND OF THE INVENTION

1. Field of the Invention

The present invention relates to a method for treating non-insulin dependent diabetes mellitus (NIDDM) in a human subject. In particular, the present invention relates to the administration of pancreatic polypeptide or the carboxyl terminal fragment of pancreatic polypeptide, either alone or in combination with insulin or an oral hypoglycemic agent to treat NIDDM by a) inhibiting stimulation of cyclic adenosine monophosphate (cAMP) by glucagon, b) inhibiting secretion of digestive enzymes from the exocrine pancreas, and/or c) potentiating the effect of leptin in reducing neuropeptide Y synthesis.

2. Background Art

NIDDM, also known as type II diabetes or maturity onset diabetes (MOD) describes a disorder, primarily in adults, characterized by fasting or post-meal hyperglycemia and most commonly associated with obesity. NIDDM is distinguished from type I diabetes or insulin dependent diabetes on the basis that the type II diabetic is not dependent on insulin for survival. Most patients diagnosed with NIDDM exhibit elevated basal insulin levels, with the degree of elevation often correlated with the degree of obesity.

Although NIDDM is correlated with resistance to insulin action, the primary defect that induces this disease has not yet been established. The metabolic dysfunctions associated with NIDDM are insulin resistance (impaired insulin sensitivity) and increased hepatic glucose output (hyperglycemia). Insulin resistance describes a pathophysiological state in which insulin does not produce the expected decrease in blood glucose concentrations. Insulin sensitivity refers to a complete or partial reversal of the insulin resistant state.

Most current therapies prescribed for treatment of NIDDM act by stimulating insulin release, which may actually be detrimental because this leads to early exhaustion of the pancreatic islets. Furthermore, high insulin levels may contribute to complications of the disease. Thus, there exists a need for a treatment of NIDDM that results in a decrease in hyperglycemia and an increase in insulin sensitivity without additional detrimental effects.

The present invention fulfills this need by providing an effective treatment of NIDDM by the administration of an amount of pancreatic polypeptide (PP) alone or in combination with other hypoglycemic agents.

SUMMARY OF THE INVENTION

The present invention provides a method of treating NIDDM in a patient diagnosed with NIDDM by administering to the patient a compound, in a pharmaceutically acceptable carrier, that reduces hepatic glucose production in the patient by inhibiting hepatic expression of the alpha subunit of a $G_s$ protein in a liver cell plasma membrane, thereby inhibiting stimulation of cAMP by glucagon, whereby the reduction in hepatic glucose production treats the NIDDM.

Also provided is a method for screening compounds for the ability to treat NIDDM comprising determining if the compound decreases hepatic expression of the alpha subunit of a $G_s$ protein in a liver cell plasma membrane, thereby inhibiting the stimulation of cAMP by glucagon, a compound which decreases the hepatic expression of the alpha subunit of the $G_s$ protein in the liver cell plasma membrane, thereby inhibiting the stimulation of cAMP by glucagon, being a compound with the ability to treat NIDDM.

The present invention further provides a kit for treating NIDDM comprising a compound in a pharmaceutically acceptable carrier that decreases hepatic expression of the alpha subunit of the $G_s$ protein in the liver cell plasma membrane, thereby inhibiting stimulation of cAMP by glucagon.

Also provided is a method for treating NIDDM in a patient diagnosed with NIDDM by administering to the patient a compound, in a pharmaceutically acceptable carrier, that inhibits beta cell and pancreatic cell hypertrophy by binding the vagal nuclear complex, thereby inhibiting secretion of digestive enzymes by the exocrine pancreas in the patient, whereby the inhibition of beta cell and pancreatic islet hypertrophy treats the NIDDM.

In addition, the present invention provides a method of screening compounds for the ability to treat NIDDM comprising determining if the compound binds the vagal nuclear complex and inhibits secretion of digestive enzymes by the exocrine pancreas, thereby inhibiting beta cell and pancreatic islet hypertrophy, a compound which binds the vagal nuclear complex and inhibits secretion of digestive enzymes by the exocrine pancreas, thereby inhibiting beta cell and pancreatic islet hypertrophy, being a compound with the ability to treat NIDDM.

Also provided is a kit for treating NIDDM comprising a compound in a pharmaceutically acceptable carrier that binds the vagal nuclear complex and inhibits secretion of digestive enzymes by the exocrine pancreas, thereby inhibiting beta cell and pancreatic islet hypertrophy.

The present invention further provides a method for treating NIDDM in a patient diagnosed with NIDDM by administering to the patient a compound, in a pharmaceutically acceptable carrier, that enhances insulin sensitivity and reverses the effects of neuropeptide Y by binding the arcuate nucleus in the hypothalamus, thereby potentiating the effect of leptin in reducing neuropeptide Y synthesis, whereby the enhancement of insulin sensitivity and reversal of the effects of neuropeptide Y treat the NIDDM.

Additionally provided is a method of screening compounds for the ability to treat NIDDM comprising determining if the compound binds the arcuate nucleus in the hypothalamus and potentiates the effect of leptin in reducing neuropeptide Y synthesis, thereby enhancing insulin sensitivity and reversing the effects of neuropeptide Y, a compound which enhances insulin sensitivity and reverses the effects of neuropeptide Y being a compound with the ability to treat NIDDM.

Furthermore, the present invention provides a kit for treating NIDDM comprising a compound in a pharmaceutically acceptable carrier that binds the arcuate nucleus in the hypothalamus and potentiates the effect of leptin in reducing neuropeptide Y synthesis, thereby enhancing insulin sensitivity and reversing the effects of neuropeptide Y.

DESCRIPTION OF THE PREFERRED EMBODIMENTS

The present invention may be understood more readily by reference to the following detailed description of specific embodiments and the Examples included herein. As used herein, "a" can included multiples.

This invention provides a method of treating NIDDM in a patient diagnosed with NIDDM by administering to the patient a compound, in a pharmaceutically acceptable carrier, that reduces hepatic glucose production in the patient by decreasing hepatic expression of the alpha subunit of a $G_s$ protein in a liver cell plasma membrane, thereby inhibiting stimulation of cAMP by glucagon in the patient, whereby the reduction in hepatic glucose production treats the NIDDM.

The primary action of glucagon (circulating hormone from pancreas) in the liver is to promote glycogenolysis (breakdown of glycogen to produce glucose) and it produces this effect by binding to its cell surface receptor, activating the heterotrimeric stimulatory G protein ($G_s$) and promoting its dissociation into a monomeric α subunit and dimeric βγ subunits. The activated $G_s$α subunit interacts with and activates adenylyl cyclase, which increases the conversion of ATP to cyclic AMP. The increase in cellular cyclic AMP activates cAMP-dependent protein kinase, which phosphorylates and activates phosphorylase kinase. Once activated, this enzyme phosphorylates and activates glycogen phosphorylase, with a net result being increased breakdown of glycogen into glucose-1-phosphate. In NIDDM, where insulin resistance compromises the normal ability of insulin to stimulate peripheral glucose uptake, glucagon's glycogenolytic effects exacerbate the existing hyperglycemia. A decrease in the ability of glucagon to stimulate cyclic AMP production results in a decrease in hepatic glucose production and has the net effect of lessening the severity of hyperglycemia associated with NIDDM.

The compound of this invention can be PP, having the amino acid sequence: Ala-Pro-Leu-Glu-Pro-Val-Tyr-Pro-Gly-Asp-Asn-Ala-Thr-Pro-Glu-Gln-Met-Ala-Gln-Tyr-Ala-Ala-Asp-Leu-Arg-Arg-Tyr-Ile-Asn-Met-Leu-Thr-Arg-Pro-Arg-Tyr-NH$_2$ (SEQ ID NO: 1), or the carboxyl terminal fragment of PP, having the amino acid sequence: Leu-Thr-Arg-Pro-Arg-Tyr-NH$_2$ (SEQ ID NO:2). Either of these compounds can be administered alone or in combination with insulin or other oral hypoglycemic compounds which enhance the function of either PP or the carboxyl terminal fragment of PP in reducing hepatic glucose production. Alternatively, the compound of the present invention can be any compound or combination of compounds that reduce hepatic glucose production, in a patient diagnosed with NIDDM, by inhibiting expression of the alpha subunit of the $G_s$ protein in the liver cell plasma membrane, thereby inhibiting stimulation of cAMP by glucagon in a patient diagnosed with NIDDM.

The present invention further provides a method for treating NIDDM in a patient diagnosed with NIDDM by administering to the patient a compound, in a pharmaceutically acceptable carrier, that inhibits beta cell and pancreatic islet hypertrophy in a patient by binding the vagal nuclear complex, thereby inhibiting secretion of digestive enzymes by the exocrine pancreas in the patient, whereby the inhibition of beta cell and pancreatic islet hypertrophy treats the NIDDM.

The ordered arrangement of the endocrine cell types within the pancreatic islet appears to be an important prerequisite for the normal insulin response to a meal. The beta cells which synthesize and secrete insulin occur as a central core in the islet and are surrounded by the other islet cell types-glucagon cell, pancreatic polypeptide cell and the somatostatin cell. The pancreatic islet and beta cell hypertrophy that occurs in maturity onset diabetes is associated with a disturbance in this ordered architecture and abnormal insulin secretion. Vagal hyperactivity leads to islet cell and beta cell hypertrophy and the early (cephalic-vagal) phase of insulin secretion is abnormal in NIDDM. It is believed that enhanced vagal tone leads to islet and beta cell hypertrophy and disordered insulin release. PP inhibits the secretion of pancreatic digestive enzymes by inhibiting vagal tone. Furthermore, circulating PP binds to specific receptors in the vagal nuclear complex. The vagal nuclear complex (VNC) lies in the midbrain and receives incoming information from the vagal nerves through the Nucleus Tractus Solitarius. The Dorsal Motor Nucleus of the vagus which is also a component of the VNC provides the "efferent" nerve fibers that stimulate early phase insulin release and digestive enzyme secretion. Furthermore, direct injection of PP into the VNC has been shown to inhibit secretion of pancreatic digestive enzymes. In whole animals, PP inhibits insulin release. It appears that PP inhibits islet cell hypertrophy and insulin release by a direct action on the VNC that results in decreased vagal tone to both the pancreatic islet that produces insulin and the pancreatic acinar tissue that produces the pancreatic digestive enzymes.

In this embodiment, either PP or the carboxy terminal fragment of PP can be administered alone or in combination with insulin or other oral hypoglycemic compounds which enhance the function of either PP or the carboxyl terminal fragment of PP in inhibiting beta cell and pancreatic islet hypertrophy. Alternatively, the compound of the present invention can be any compound or combination of compounds that inhibit beta cell and pancreatic islet hypertrophy in a patient diagnosed with NIDDM by binding the vagal nuclear complex and inhibiting secretion of digestive enzymes by the exocrine pancreas in a patient diagnosed with NIDDM.

Additionally provided in the present invention is a method for treating NIDDM in a patient diagnosed with NIDDM by administering to the patient a compound, in a pharmaceutically acceptable carrier, that enhances insulin sensitivity and reverses the effect of neuropeptide Y (NPY) in a patient by binding the arcuate nucleus in the hypothalamus, thereby potentiating the effect of leptin in reducing NPY synthesis in the patient, whereby the enhancement of insulin sensitivity and reversal of the effects of NPY treat the NIDDM.

NPY is a neurotransmitter that is structurally related to pancreatic polypeptide. When injected directly into the brain, it is the most potent stimulant to trigger eating known. Indeed it is the only peptide that, when injected repeatedly into the brain, causes hyperphagia and obesity. NPY also acts through the VNC and vagus nerve to stimulate cephalic phase insulin release. Leptin is a peptide released by fat cells which inhibits NPY synthesis by an effect on the arcuate nucleus in the hypothalamus. PP likely also inhibits NPY synthesis via an action on the PP receptors recently identified in the arcuate nucleus. As such it would inhibit the ability of NPY to initiate cephalic phase and stimulate early phase insulin release by both inhibiting NPY synthesis and decreasing the stimulatory effects of NPY on the VNC.

Current data suggest that increased Neuropeptide Y (NPY) synthesis in the arcuate nucleus in the brain causes enhanced food intake, increased vagal tone and decreased sympathetic tone; these are features that characterize obesity and diabetes. High vagal tone leads to inappropriate insulin and glucagon release which coupled with hyperphagia contributes to insulin resistance, obesity and diabetes. The data suggest that Pancreatic Polypeptide (PP) reverses this syndrome by decreasing vagal tone, decreasing insulin release and hepatic glucose production, thereby enhancing insulin sensitivity. Insulin stimulates leptin release from isolated adipocytes. Thus, PP is expected to inhibit leptin release in the whole animal. Furthermore, PP treatment is expected to inhibit NPY mRNA expression in the arcuate nucleus based on the demonstration of a novel PP receptor population in the hypothalamus using receptor autoradiography. Receptor localization in the arcuate nucleus using these techniques provides a mechanism to identify hormones and neurotransmitters that would be expected to alter food intake and nutrient metabolism by effects on NPY. NPY message and peptide levels can be measured directly using methods described in the references on the attached sheet. Although much attention has been focused recently on leptin, leptin therapy of obesity may not be beneficial because of leptin resistance. Given PP's lack of side effects even in supramaximal doses, PP has the potential to be a more viable and safe method of treating the obese, diabetic patient. PP appears to complete a series of negative feedback loops that serves to control body weight and glucose metabolism by modulating insulin release acutely and NPY synthesis chronically. These PP feedback loops are impaired in diabetics because of decreased secretion rather than down regulation of the receptor or impaired signal transduction. First PP can act through receptors recently identified in the arcuate nucleus to inhibit NPY synthesis. This would lead to decreased food intake, particularly decreased intake of carbohydrate rich foods. In addition NPY increases vagal tone acting through neural tracts that pass through the paraventricular nucleus (PVN) to the Vagal Nuclear Complex (VNC) in the brainstem. There are PP receptors in the PVN and the VNC which provides multiple sites for PP to inhibit vagal tone. Indeed, PP injected directly into the Dorsal Motor Nucleus of the vagus (a component of the VNC) does inhibit the vagus. Inhibition of vagal tone to the pancreatic islets would explain PP's ability to inhibit insulin release. When this is coupled to inhibition of hepatic glucose production (mediated by the PP receptors in the liver) insulin sensitivity is enhanced and an improvement in the diabetes is observed. PP treatment would have the added benefit that it would also decrease body weight. As obesity frequently accompanies maturity onset (Type II) diabetes a double benefit would be experienced by these patients.

In this embodiment, either PP or the carboxy terminal fragment of PP can be administered alone or in combination with insulin or other oral hypoglycemic compounds which enhance the function of either PP or the carboxyl terminal fragment of PP in enhancing insulin sensitivity and reversing the effects of neuropeptide Y. Alternatively, the compound of the present invention can be any compound or combination of compounds that enhances insulin sensitivity and reverses the effects of neuropeptide Y in a patient diagnosed with NIDDM by binding the arcuate nucleus in the hypothalamus and potentiating the effect of leptin in reducing neuropeptide Y synthesis in a patient diagnosed with NIDDM. "Syndrome X" describes a constellation of abnormal lipid profile, atherosclerosis and heart disease associated with and possibly caused by the insulin resistant state. PP treatment would also be expected to be beneficial in "Syndrome X" and other insulin resistant states. Complications of NIDDM such as renal failure, diabetic retinopathy, atherosclerosis, cardiovascular disease and neuropathy could be delayed or made less severe by treatment with PP. PP reverses the insulin resistant state, thus establishing a state of insulin sensitivity.

The PP and carboxyl terminal fragment of PP can be obtained by standard procedures known in the art and are also available from commercial sources (e.g., Peninsula Labs, Belmont, Calif.). Recombinant human insulin can be obtained either commercially (e.g. Eli Lilly, Indianapolis, Ind.), or by standard procedures known in the art.

The PP can be administered in a range between 2 and 500 $\mu$g/kg of body weight/day, preferably in a range between 4 and 100 $\mu$g/kg of body weight/day and most preferably in a dosage of 12 $\mu$g/kg body weight/day. Chemical alteration of the peptide, as described below, could lead to longer acting analogs (e.g. substitution of D-amino acids, etc.), requiring even lower dosages such as for example, between 0.5 and 50 $\mu$g/kg of body weight/day. This amount can be administered as a single dose or divided into several doses to be administered over a 24 hour period. The exact dosage may vary on the basis of the patient's age, weight, size and general overall condition and a physician would best be able to determine the exact dosage according to these parameters. Further guidance on determining dosages and modes of administration are available as provided in Remington's Pharmaceutical Sciences (13).

Analogs of PP and of the carboxyl terminal fragment of PP can also be administered to patients to treat NIDDM. Such analogs can include, but are not limited to, compounds having the chemical composition of PP or the carboxyl terminal fragment of PP, wherein D-amino acids have been incorporated into the molecule. Such analogs would be anticipated to have a longer acting effect in humans than PP and the carboxyl terminal fragment of PP and would, thus, be administered in lower doses. For example, a substitution of a D-amino acid at the amino terminal of the carboxyl terminal fragment of PP would protect the peptide from enzymatic degradation:

D-Leu-Thr-Arg-Pro-Arg-Tyr-NH2 (SEQ ID NO:3). Other examples of D-amino acid substitutions than can be beneficial are:

D-Leu-Thr-Arg-Pro-D-Arg-Tyr-NH$_2$ (SEQ ID NO:4) and Leu-Thr-Arg-Pro-D-Arg-Tyr-NH$_2$(SEQ ID NO:5).

The carboxyl terminal fragment of PP can be administered to a patient diagnosed with NIDDM in a range between 20 and 5,000 $\mu$g/kg of body weight/day, more preferably in a range of 40 to 1,000 $\mu$g/kg of body weight/day and most preferably in a dosage of 200 $\mu$g/kg of body weight/day. Chemical alteration of the fragment of PP could lead to longer acting analogs (e.g. substitution of D-amino acids, etc.), requiring even lower dosages such as for example, between 1 and 1,000 $\mu$g/kg of body weight/day. This amount can be administered as a single dose or divided into several doses to be administered over a 24 hour period. The exact dosage may vary on the basis of the patient's age, weight, size and general overall condition and a physician would best be able to determine the exact dosage according to these parameters. Further guidance on determining dosages and modes of administration are available as provided in Remington's Pharmaceutical Sciences (13).

PP and carboxyl terminal fragments and analogs could be administered with injectable insulin or with other hypoglycemic agents. These include, but are not limited to, oral hypoglycemic compounds such as the sulfonylureas and the biquanides. The sulfonylureas can include, but are not limited to, Tobutanine (Orinase) Acetohexamide (Dymelor), Tolazanide (Tolinase) and Chloropropramide (Diabenase). Biquanides can include, but are not limited to, glyburide, glopizide and metformin.

The compounds administered to treat NIDDM can be administered orally and/or parenterally in a pharmaceutically acceptable carrier to human subjects. The preferable mode of administration would be by subcutaneous injection. Transnasal and transdermal administrations or any other oral or parenteral route are other potential modes of administration. Suitable carriers for use in the present invention include, but are not limited to, pyrogen-free saline. For parenteral administration of the compounds, a sterile solution or suspension is prepared in saline that may contain additives, such as ethyl oleate or isopropyl myristate, and can be injected, for example, into subcutaneous or intramuscular tissues.

Suitable carriers for oral administration of compounds to treat NIDDM can include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pharmaceutically accepted oils, or a mixture of both. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel. The compounds may be contained in enteric coated capsules that release the compounds into the intestine to avoid gastric breakdown.

Alternatively, the compounds may be microencapsulated with either a natural or a synthetic polymer into microparticles 4–8 $\mu$m in diameter, which target intestinal lymphoid tissues and produce a sustained release of compounds for up to four weeks (14, 15).

This invention further provides a method of screening substances for the ability to treat NIDDM, comprising determining if the compound is an inhibitor of the expression of the alpha subunit of the $G_s$ proteins in the liver cell plasma membrane, thereby inhibiting the stimulation of cAMP by glucagon, a compound which inhibits the expression of the alpha subunit of the $G_s$ proteins in the liver cell plasma membrane, thereby inhibiting the stimulation of cAMP by glucagon, being a compound with the ability to treat NIDDM. For example, the compound can be administered to an appropriate animal model as described below and the efficacy of the compound in inhibiting the ability of glucagon to activate cyclic AMP can be determined according to the experimental protocols set forth in the Examples herein.

The present invention further provides a method of screening compounds for the ability to treat NIDDM, comprising determining if the compound binds the vagal nuclear complex and inhibits secretion of digestive enzymes by the exocrine pancreas, thereby inhibiting beta cell and pancreatic islet hypertrophy. A compound which binds the vagal nuclear complex and inhibits secretion of digestive enzymes by the exocrine pancreas inhibits beta cell and pancreatic islet hypertrophy is a compound with the ability to treat NIDDM. For example, the compound can be administered to an appropriate animal model as described below and the efficacy of the compound in binding the vagal nuclear complex and inhibiting secretion of digestive enzymes by the exocrine pancreas can be determined according to the experimental protocols set forth in the Examples herein. Assays for determining the ability of a compound to bind the vagal nuclear complex are known in the art.

Also provided in the present invention is a method of screening compounds for the ability to treat NIDDM, comprising determining if the compound binds the arcuate nucleus in the hypothalamus and potentiates the effect of leptin in reducing NPY synthesis, thereby enhancing insulin sensitivity and reversing the effects of NPY. A compound which enhances insulin sensitivity and reverses the effects of NPY can be used to treat NIDDM. For example, the compound can be administered to an appropriate animal model as described below and the efficacy of the compound in binding the arcuate nucleus in the hypothalamus and potentiating the effect of leptin in reducing NPY synthesis can be determined according to the experimental protocols set forth in the Examples herein. Assays that can be used to determining the ability of PP and other compounds to effect NPY synthesis in the arcuate nucleus and PVN are known in the art. For example, methods that could be used to measure NPY levels in specific regions of the brain after PP treatment (arcuate nucleus and PVN) are included in references 23–29. Methods that could be used to measure NPY message levels in specific regions of the brain are also included in references (25–27).

The preferred animal models that could be used for screening for the efficacy of various compounds to treat NIDDM include but are not limited to: 1) the fatty Zucker (fa/fa) rat, 2) the ob/ob mouse, 3) the db/db mouse, as well as any other suitable animal model of hyperglycemia, obesity and impaired insulin function now known or developed in the future. These models are produced by recessive inheritance of a single gene (1,5,8,9). Other models can include 1) a diet-induced obesity rodent model, wherein specific strains of rodents are fed a high fat or "cafeteria" type diet, 2) a VMH-lesioned animal model and an animal model wherein repeated injections of NPY are given by indwelling cannula into the cerebroventricular system of the brain, and 3) humans diagnosed with NIDDM.

In another embodiment, the present invention provides a kit for treating NIDDM comprising a compound in a pharmaceutically acceptable carrier that inhibits the expression of the alpha subunit of the $G_s$ proteins in the liver cell plasma membrane, thereby inhibiting the stimulation of cAMP by glucagon.

A kit for treating NIDDM is also provided, comprising a compound in a pharmaceutically acceptable carrier that binds the vagal nuclear complex and inhibits secretion of digestive enzymes by the exocrine pancreas, and beta cell and pancreatic islet hypertrophy.

Additionally, the present invention provides a kit for treating NIDDM comprising a compound in a pharmaceutically acceptable carrier that binds the arcuate nucleus in the hypothalamus and potentiates the effect of leptin in reducing neuropeptide Y synthesis, thereby enhancing insulin sensitivity and reversing the effects of neuropeptide Y.

The compound of the kit can be PP or the carboxyl terminal fragment of PP, either alone or in combination with insulin or other oral-hypoglycemic agents. Alternatively, the compound of the kit can be a compound determined to have the ability to treat NIDDM, according to the protocols taught in the Examples herein.

The following Examples are intended to illustrate, but not limit, the invention. While the protocols described are typical of those that might be used, other procedures known to those skilled in the art may be alternatively employed.

EXAMPLES

Experimental Animal Protocol. Lean (+/?) and fatty (fa/fa) Zucker rats were obtained from Harlan Labs at seven weeks of age and randomly assigned to two groups within each phenotype. One group was injected subcutaneously with PP (Peninsula Labs (Belmont, Calif.) (200 $\mu$g/day/kg body weight) in a vehicle of physiological saline (0.9% w/v) while the other group was injected with only vehicle. The two groups within each phenotype received their respective treatments for five days, after which the animals were weighed and sacrificed following an overnight fast. Blood samples were obtained from each animal for assays of plasma glucose and insulin according to standard methods known in the art (3) and the pancreas was removed and subjected to an acid-ethanol extraction (0.1N HCl, 70% ethanol) as described previously for assay of pancreatic insulin (3). Livers were removed into ice cold balanced salt solution. After cooling, each liver was cleaned of connective tissue and minced into 2–4 mm pieces with scissors in 5 ml of ice-cold homogenizing buffer (50 mM Hepes, pH 6.5, 5 mM EDTA, 3 mM orthophenanthroline, 0.2 $\mu$M iodoacetic acid, 1 mM PMSF, 25 $\mu$m leupeptin (3). The minced liver was homogenized in a 40 ml Dounce homogenizer in 25 ml of homogenizing buffer with 25 strokes of the loose pestle and three strokes of the tight pestle. The homogenate was centrifuged for five minutes at 3000×g. The supernatant was removed and centrifuged for 20 min at 16,000×g. The resulting pellet was retained, resuspended in phosphate buffered saline (PBS) containing 5 mM MgCl$_2$ and homogenized with five strokes of the Dounce homogenizer. After centrifuging for 20 min at 16,000×g, the membrane pellet was resuspended in homogenizing buffer containing 0.1% bovine serum albumin (BSA). Aliquots were frozen in liquid nitrogen and stored at –80° C.

Preparation of PP and the carboxyl terminus of PP. Highly purified PP and the C-terminal hexapeptide of PP were obtained from commercial sources.

Glucagon binding in liver membranes. Glucagon was radioiodinated using chloramine T and purified by C-18 reverse phase HPLC. In brief, 25 $\mu$g of glucagon was incubated with 1 mCi of carrier free Na$^{125}$I in the presence of 1 $\mu$g chloramine T for 30 seconds. The reaction was terminated with 2 $\mu$g sodium metabisulfite, followed by purification of monoiodinated glucagon by HPLC. The labeled glucagon was diluted with an equal volume of 25 mM Tris buffer (pH 7.4) containing 1% BSA and stored at 4° C. prior to use. The glucagon receptor binding assay was conducted by a modification of the procedure of Lin et al. (12) in a final volume of 500 $\mu$l. Saturation binding experiments were conducted with 25 $\mu$g of liver plasma membranes and 10–5000 pM radiolabeled glucagon. The samples were incubated for one hour at 30° C., and membrane bound glucagon was isolated by centrifugation at 40,000×g for ten minutes. Non-specific binding was assayed at each ligand concentration by including 1 $\mu$M unlabeled glucagon and was determined to average 10–20%. Competition binding curves were conducted using 50 pM labeled glucagon. Binding curves were analyzed using nonlinear least squares.

Saturation binding studies provided no evidence that the total number of glucagon binding sites differed between phenotype (lean control B$_{max}$=475±23 fmol/mg; fatty control B$_{max}$=471±44 fmol/mg). In addition, treatment with PP failed to alter total glucagon binding sites in either phenotype (fatty PP B$_{max}$=569±45 fmol/mg). The confidence intervals for the means in question are: 475±23 fmol/mg, 95% CI (420.1 to 529.9 fmol/mg) lean control group; 471±44 fmol/mg, 95% CI (366.2 to 576.0 fmol/mg) fatty control group; and 569±45 fmol/mg, 95% CI (462.3 to 676.8 fmol/mg) fatty PP group. The same conclusion was reached after analysis of binding data from a second experiment. The data from both experiments indicate that the differences in efficacy of glucagon in activating adenylyl cyclase to form cAMP between the phenotypes and its modulation by PP treatment are probably not the result of differences in glucagon receptor expression. Notwithstanding these similarities, the Scatchard plots suggest that binding affinities for glucagon may differ among the groups. However, comparison of estimates of K$_d$ among the groups (lean control: 0.39±0.16 nM; fatty control: 0.85±0.19 nM; fatty PP: 1.70±0.25 nM) produced wide confidence intervals and precluded detection of treatment differences.

A more rigorous test for group differences in binding affinity was provided by competition binding experiments with 50 pM labeled glucagon in the presence and absence of GTP. The K$_d$ values estimated using this method did not differ among the groups (lean control: 0.49±0.06 nM; fatty control: 0.86±0.09 nM; fatty PP: 0.66±0.09 nM). This approach also provides estimates of the proportion of receptors existing in high versus low affinity states and revealed that the percentage of high affinity binding sites in the fatty control group was elevated (68%) compared to the lean control group (53%). This phenotypic difference was not altered by treatment with PP (lean PP: 55% high affinity; fatty PP: 71% high affinity). These data indicate that a decrease in the total number of glucagon receptors is not the mechanism of PP's effects on the efficacy of glucagon to activate cyclic AMP.

Receptor dependent labeling of hepatocyte G proteins with 4-Azidoanilido-α[$^{32}$P]GTP. The protocol for labeling G proteins with AA-GTP was as described previously (11). The AA-[32P]-GTP used in the labeling experiments was prepared according to the protocol of Offermans et al. (6,7).

The purpose of these labeling studies was to determine whether PP stimulated the binding of AA-[$^{32}$P]GTP to proteins migrating at the known molecular weight of G proteins in liver plasma membranes. Angiotensin II was used as a positive control because it has been shown to couple to pertussis-sensitive G proteins (16). Incubation of liver plasma membranes with 1 $\mu$M angiotensin II produced a two-fold increase in labeling of G protein(s) migrating at 41 kDa on SDS PAGE gels The 41 kDa band represents the pertussis-sensitive G protein family that is expressed in hepatocytes and which couples to angiotensin II receptors.

Experiments of comparable design using PP instead of angiotensin II illustrated that PP also produces a concentration-dependent increase in labeling of G proteins migrating at 41 kDa. The maximal increase in labeling was approximately two-fold and was comparable to the maximal effect seen with angiotensin II. The data describing PP dependent labeling of liver G proteins with AA-[$^{32}$P]GTP illustrate early steps in the PP signaling cascade. The intervening steps between PP dependent G protein activation and decreased efficacy of glucagon have not been determined.

Adenylyl Cyclase Assay. Adenylyl cyclase activity leading to the production of cAMP was determined in liver plasma membranes by methods previously described (2, 4). Briefly, 25 $\mu$g of liver plasma membranes were incubated for ten minutes at 30° C. in a buffer containing 50 mM TES (pH 7.4), 4.0 mM MgCl$_2$, 2 mM creatine phosphate, 25 U/ml creatine phosphokinase, 100 $\mu$M ATP and 10 $\mu$M GTP. The reaction was conducted in a final volume of 300 $\mu$l and initiated by adding 50 $\mu$l of the membrane preparation to each incubation tube. Reactions were terminated by adding 50 $\mu$l of cold 25% TCA and centrifuging for 15 min at 3000 rpm. Cyclic AMP formed in the reaction was measured in the supernatant by radioimmunoassay according to methods described previously (2, 4). Dose-response curves were characterized using the four parameter logistic ogive in relation to log dose as described previously (2, 4).

Glucagon produced a concentration-dependent activation of adenylyl cyclase in liver plasma membranes from all four experimental groups. The response curve for the lean group treated with PP was similar to the control lean group. The estimated potencies did not differ among the groups and ranged from 5–15 nM in five experimental replicates. Maximal adenylyl cyclase activation by glucagon was much higher in fatty than in lean Zucker rats (58.1±4.4 vs. 36.4±1.8 pmol cAMP/min/mg membrane protein).

Treatment of lean rats with PP did not modify the efficacy of glucagon in liver membranes. In contrast, treatment of fatty Zucker rats with PP as described above for five days produced a significant decrease in the efficacy of glucagon in activating adenylyl cyclase, reducing the maximal adenylyl cyclase activation to levels not different from lean Zucker rats. A second replicate of this experiment with additional animals produced a similar decrease in maximal adenylyl cyclase activation in PP treated fatty Zucker rats (60.2±1.5 pmol cAMP/min/mg) compared to vehicle-treated fatty Zucker rats (87.6±1.8 pmol cAMP/min/mg). These results indicate that livers from fatty Zucker rats are hyper-responsive to glucagon compared to their lean litter mates. These studies further demonstrate that chronic treatment of fatty Zucker rats with PP (i.e., treatment for five days), as described above, corrects the hyper-responsiveness of fatty Zucker rats to glucagon.

Western Blot assay of $G_s\alpha$. Antibodies were generated against the C-terminal decapeptide (aa 345–354) of $G_s\alpha$ conjugated to keyhole limpet cyanin (KLH) via a cysteine placed on the N-terminal end of each peptide (18). Rabbits were immunized with the conjugate according to the method of Green et al. (17). The anti-$G_s\alpha$ serum was desalted using Sephadex G-25 and the G class of immunoglobulins (IgG) was purified by HPLC using a Protein A affinity column (Rainin Instr. Co., Woburn, Mass.).

Purified liver plasma membranes were solubilized on ice for one hour in 20 mM Tris, 1 mM EDTA, 1 mM DTT, 100 mM NaCl and 0.9% sodium cholate (pH 8.0). The supernatant was collected after centrifugation at 13,000×g for five minutes at 4° C. Solubilized plasma membranes were resolved by SDS polyacrylamide gel electrophoresis (12.5% acrylamide, 0.051% N,N'-diallyltartatdiamide (DATD)) and transferred to Immobilon-P PVDF membranes (Millipore Corp., Bedford, Mass.) (19,21). Following the procedure of Mumby (20), the PVDF membranes were probed with $G_s\alpha$ IgG and the bands were detected with $^{125}$I-labeled goat anti-rabbit IgG ($1.0\times10^6$ cpm/ml). The membranes were washed, blotted dry and exposed to Kodak XAR film with intensifying screens overnight.

In performing the Western blot assays, protein was carefully measured in the liver plasma membrane supernatant to assure that equal amounts of soluble membrane protein would be loaded from the respective treatment groups. The membrane preparations were blotted for the presence of $G_s\alpha$ to test for differences in expression level of the G protein that couples glucagon receptors to adenylyl cyclase in liver membranes. The Western blot data obtained showed that $G_s\alpha$ expression was significantly higher in membranes from fatty Zucker rats compared to their lean litter mates. Assuming increased complex formation of G proteins with glucagon receptors, this result could explain the increased proportion of receptors in the high afinity binding state in liver membranes from fatty rats compared to lean rats. Furthermore, while $G_s\alpha$ expression was not altered by exogenous PP in lean rats, treatment of fatty Zucker rats with PP decreased hepatic expression of $G_s\alpha$ to levels similar to that seen in lean rats. These results indicate that increased expression of $G_s\alpha$ may be the explanation for the enhanced efficacy of glucagon in fatty Zucker rats in activating adenylyl cyclase to produce hepatic glucose. These results indicate that exogenous PP appears to correct this hyper-responsiveness by altering G protein expression in the liver.

Screening of compounds for the ability to treat NIDDM by inhibiting the ability of glucagon to activate cAMP. Compounds can be screened for the ability to treat NIDDM by administering the compound to lean and fatty Zucker rats or to ob/ob mice, db/ob mice or other animals suitable as models of hyperglycemia, obesity and impaired insulin function and their lean counterparts and assaying the efficacy of the compound in inhibiting the expression of the alpha subunit of the $G_s$ protein in the liver cell plasma membrane, thereby inhibiting the ability of glucagon to activate cAMP, according to the experimental protocols set forth in the Examples herein. The plasma insulin and glucose levels of these animals can also be determined following administration of the compound to be screened. A compound shown by the methods taught herein to reduce the hyperglycemia and hyperinsulinemia in the animal models employed by inhibiting the expression of the alpha subunit of the $G_s$ protein in the liver cell plasma membrane and inhibiting the ability of glucagon to activate cAMP, thereby inhibiting hepatic glucose production, is determined to be a compound effective in treating NIDDM.

Screening of compounds for the ability to treat NIDDM by inhibiting beta cell and pancreatic islet hypertrophy. Compounds can be screened for the ability to treat NIDDM by administering the compound to lean and fatty Zucker rats or to ob/ob mice, db/ob mice or other animals suitable as models of hyperglycemia, obesity and impaired insulin function and their lean counterparts and assaying the efficacy of the compound in binding the vagal nuclear complex and inhibiting the secretion of digestive enzymes by the exocrine pancreas, according to the experimental protocols set forth in the Examples herein. The plasma insulin and glucose levels of these animals can also be determined following administration of the compound to be screened. A compound shown by the methods taught herein to reduce the hyperglycemia and hyperinsulinemia in the animal models employed by binding the vagal nuclear complex and inhibiting secretion of digestive enzymes by the exocrine pancreas, thereby inhibiting beta cell and pancreatic islet hypertrophy, is determined to be a compound effective in treating NIDDM.

Screening of compounds for the ability to treat NIDDM by enhancing insulin sensitivity and reversing the effects of neuropeptide Y. Compounds can be screened for the ability to treat NIDDM by administering the compound to lean and fatty Zucker rats or to ob/ob mice, db/ob mice or other animals suitable as models of hyperglycemia, obesity and impaired insulin function and their lean counterparts and assaying the efficacy of the compound in binding the arcuate nucleus in the hypothalamus, thereby potentiating the effect of leptin in reducing neuropeptide Y synthesis, according to the experimental protocols set forth in the Examples herein. The plasma insulin and glucose levels of these animals can also be determined following administration of the compound to be screened. A compound shown by the methods taught herein to reduce the hyperglycemia and hyperinsulinemia in the animal models employed by binding the arcuate nucleus in the hypothalamus and potentiating the effect of leptin in reducing neuropeptide Y synthesis, thereby enhancing insulin sensitivity and reducing the effects of neuropeptide Y, is determined to be a compound effective in treating NIDDM.

Protocols for administration of PP or carboxyl terminal fragments of PP to humans diagnosed with NIDDM. To treat NIDDM in a human subject, a protocol for human administration modeled after the one used by Bernston et al. (22) can be used. For example, between 2 and 500 µg/kg body weight/day of PP and preferably between 4 and 100 µg/kg body weight/day of PP can be intravenously infused into a subject over two 90 minute periods per day for about two days or until the symptoms of NIDDM, e.g., hyperglycemia and hyperinsulinemia, subside, either alone or in combination with insulin or other oral hypoglycemic agents administered in dosages known to be effective in reducing blood glucose levels.

Alternatively, between 20 and 5,000 μg/kg body weight/day of the carboxyl terminal fragment of PP and preferably between 40 and 1,000 μg/kg body weight/day of the carboxyl terminal fragment of PP can be intravenously infused into a subject over two 90 minute periods per day for about two days or until the symptoms of NIDDM, e.g., hyperglycemia and hyperinsulinemia, subside, either alone or in combination with insulin or other oral hypoglycemic agents administered in dosages known to be effective in reducing blood glucose levels.

If analogs of PP or of the carboxyl terminal fragment of PP containing D-amino acid substitutions are available, between 0.5 and 50 μg/kg body weight/day of PP analog or between 1 and 1,000 μg/kg body weight/day of PP carboxyl terminal fragment analog can be intravenously infused into a subject over two 90 minute periods per day for about two days or until the symptoms of NIDDM, e.g., hyperglycemia and hyperinsulinemia, subside, either alone or in combination with insulin or other oral hypoglycemic agents administered in dosages known to be effective in reducing blood glucose levels.

When PP or carboxyl terminal fragments of PP are administered in combination with insulin or other hyperglycemic compounds, the dosage range for PP can be from 1 to 100 μg/kg body weight/day and from 10 to 1,000 μg/kg body weight/day for carboxyl terminal fragments of PP.

The subject's plasma glucose and insulin levels can be measured according to protocols standard in the art. For example, a glucose tolerance test can be performed for each subject before the first infusion, during the last infusion and 24 hours after the last infusion. Levels of insulin, C Peptide, PP, glucagon and blood glucose as well as body weight can also be monitored throughout the period before, during and after infusion, according to protocols standard in the art.

In addition, PP, the carboxyl terminal fragment of PP or D-amino acid analogs of these compounds can be administered as a subcutaneous infusion given twice a day. Preliminary dose studies would be carried out by starting with a dosage of 2 μg/kg and doubling this dosage until the optimal dosage for a given subject was determined as indicated by measuring the subject's glucose tolerance and insulin secretion levels. After the optimal daily dosage is determined, the subject can receive injections, for example, twice daily for two or three days. The optimal daily dosage, once determined, can be administered daily or intermittently as needed, according to the subject's blood glucose and insulin levels. Levels of insulin, C Peptide, PP, glucagon and blood glucose levels can be monitored throughout the period before, during and after infusion, according to protocols standard in the art.

Throughout this application various publications are referenced. The disclosures of these publications in their entireties are hereby incorporated by reference into this application in order to more fully describe the state of the art to which this invention pertains.

REFERENCES

1. Bray, G. A. 1977. The Zucker-fatty rat: a review. *Fed Proc.* 36:148–153.
2. Gettys, T. W., P. M. Burrows and D. M. Henricks. 1986. Variance weighting functions in radioimmunoassay calibration. *Am. J Physiol* 251:E357–E361.
3. Gettys, T. W., R. Garcia, K. Savage, D. C. Whitcomb, S. Kanayama and I. L. Taylor. 1991. Insulin sparing effects of pancreatic polypeptide in congenitally obese rodents. *Pancreas* 6:46–53.
4. Gettys, T. W., K. Okonogi, W. C. Tarry, J. Johnston, C. Horton and I. L. Taylor. 1990. Examination of relative rates of cAMP synthesis and degradation in crude membranes of adipocytes treated with hormones. *Second Messengers and Phosphoproteins* 13:37–50.
5. Bray, G. A. and D. A. York. 1979. Genetically transmitted obesity in rodents. *Physiol. Rev.* 51:598–646.
6. Offermanns, S., R. Schafer, B. Hoffman, E. Bombien, K. Spicher, K. D. Hinsch, Schultz and W. Rosenthal. 1990. Agonist-sensitive binding of a photoreactive GTP analog to a G-protein alpha-subunit in membranes of HL-60 cells. *FEBS Lett.* 260:14–18.
7. Offermans, S., G. Schultz and W. Rosenthal. 1991. Identification of receptor-activated G proteins with photoreactive GTP analog [alpha-32P]GTP azidoanilide. *Methods Enzymol* 195:286–301.
8. Kasiske, B. L., M. P. O'Donnell and W. F. Keane. 1992. The Zucker rat model of obesity, insulin resistance, hyperlipidemia and renal injury. *Hypertension* 19 Suppl. I:I110–I115.
9. Bray, G. A. 1992. Pathophysiology of obesity. *Am. J. Clin. Nutr.* 55 Suppl. 488S–494S.
10. Gettys, T. W. and J. D. Corbin. 1989. The protein kinase family of enzymes. In: Receptor Phosphorylation. V. K. Moudgil, editor. CRC Press, Boca Raton, Fla. pp.39–88.
11. Gettys, T. W., T. A. Fields and J. R. Raymond. 1994. Selective activation of inhibitory G protein alpha-subunits by partial agonists of the human 5-HT1A receptor. *Biochemistry* 33:4283–4290.
12. Lin, M. D., D. E. Wright, V. J. Jruby and M. Rodbell. 1975. Structure-function relationships in glucagon: properties of highly purified Des-His$^1$-, monoiodo-, and [Des-Asn$^{28}$, Thr$^{29}$] (homoserine lactone$^{27}$)-glucagon. *Biochemistry* 14:1559–1563.
13. Martin, E. W. (ed.) *Remington's Pharmaceutical Sciences,* latest edition Mack Publishing Co., Easton, Pa.
14. Eldridge et al. 1989. *Cur. Topics in Microbiol. and Immunol.,* 146:59–65.
15. Oka et al. 1990. *Vaccine,* 8:573–576.
16. Lynch, C. J., P. F. Blackmore, E. H. Johnson, R. L. Wange, P. K. Krone and J. H. Exton. 1989. Guanine nucleotide binding regulatory proteins and adenylate cyclase in livers of streptozotocin- and BB/Wor-diabetic rats. *J. Clin. Invest.* 83:2050–2062.
17. Green, N., H. Alexander, A. Olson, S. Alexander, T. M. Shinnick, J. G. Sutcliffe and R. A. Lerner. 1982. Immunogenic structure of the influenza virus hemagglutinin. *Cell* 28:477–487.
18. Raymond, J. R., C. L. Olsen and T. W. Gettys. 1993. Cell-specific physical and functional coupling of human 5-HT1A receptors to inhibitory G protein alpha-subunits and lack of coupling to $G_s$-alpha. *Biochemistry* 32:11064–11073.
19. Gettys, T. W., V. Ramkumar, R. J. Uhing, L. Seger and I. L. Taylor. 1991. Alterations in mRNA levels, expression and function of GTP-binding regulatory proteins in adipocytes from obese mice (C57BL/6J-ob/ob). *J. Biol. Chem.* 266:15949–15955.
20. Mumby, S., I.-K. Pang, A. G. Gilman and P. C. Sternwiess. 1988. Chromatographic resolution and immunologic identification of the alpha-40 and alpha-41 subunits of guanine nucleotide-binding regulatory proteins. *J. Biol. Chem.* 263:2020–2026.

21. Uhing, R. J., P. G. Polakis and R. Snyderman. 1987. Isolation of CTP-binding proteins from myeloid HL-60 cells. *J. Biol. Chem.* 262:15575–15579.
22. Bernston, G. G., W. B. Zipf, T. M. O'Dorisio, J. A. Hoffman and R. E. Chance. 1993. Pancreatic polypeptide infusions reduce food intake in Prader-Willi syndrome. *Peptides* 14:497–503.
23. Sanacora G, Kershaw M. Finkelstein J A, White J D. 1990. Increased hypothalamic content of preproneuropeptide Y messenger ribonucleic acid in genetically obese Zucker rats and its regulation by food deprivation. Endocrinology 127: 730–737.
24. White J D, Olchovsky D, Kershaw M, Berelowitz M, Berelowitz M. 1990. Increased hypothalamic content of preproneuropeptide-Y messenger ribonucleic acid in streptozotocin-diabetic rats. Endocrinology 126:765–772.
25. Brady L S, Smith M A, Gold P W, Herkenham M. 1990. Altered expression of hypothalamic neuropeptide Y mRNAs in food-restricted and food-deprived rats. Neuroendocrinology 52:441–447.
26. Chau S C, Leibel R L, Hirsch J. 1991. Food deprivation and age modulate neuropeptide gene expression in the murine hypothalamus and adrenal gland. Mol. Brain Res. 9:95–101.
27. O'Shea R D, Gundlach A L. 1991. Preproneuropeptide Y messenger Ribonucleic acid in the hypothalamic arcuate nucleus of the rat is increased in food deprivation or dehydration. J. Neuroendocrinol. 3:11–14.
28. Dean R G, White B D. 1990. Neuropeptide Y expression in rat brain: Effects of adrenalectomy. Neurosci. Lett. 114:339–344.
29. Beck B, Stricker-Krongrad A, Burlet A, Nicolas J-P, Burlet C. 1990. Influence of diet composition on food intake and hypothalamic neuropeptide Y (NPY) in the rat. Neuropeptides 17:197–203.

What is claimed is:

1. A method for treating non-insulin dependent diabetes mellitus in a patient diagnosed with non-insulin dependent diabetes mellitus by administering to the patient a composition comprising a compound selected from the group consisting of pancreatic polypeptide and the carboxyl terminal fragment of pancreatic polypeptide having the amino acid sequence of SEQ ID NO: 2 in a pharmaceutically acceptable carrier, that reduces hepatic glucose production in the patient by decreasing hepatic expression of the alpha subunit of a $G_s$ protein in a liver cell plasma membrane, thereby inhibiting stimulation of cyclic adenosine monophosphate by glucagon in the patient, whereby the reduction in hepatic glucose production treats the non-insulin dependent diabetes mellitus.

2. The method of claim 1, wherein the compound is pancreatic polypeptide.

3. The method of claim 2, wherein the composition further comprises insulin.

4. The method of claim 2, wherein the composition further comprises an oral hypoglycemic agent.

5. The method of claim 4, wherein the oral hypoglycemic agent is selected from the group consisting of Tobutanine, Acetohexamide, Tolazanide, Chloropropramide, glyburide, glopizide and metformin.

6. The method of claim 1, wherein the compound is the carboxyl terminal fragment of pancreatic polypeptide having the amino acid sequence of SEQ ID NO:2.

7. The method of claim 6, wherein the composition further comprises insulin.

8. The method of claim 6, wherein the composition further comprises an oral hypoglycemia agent.

9. The method of claim 8, wherein the oral hypoglycemic agent is selected from the group consisting of Tobutanine, Acetohexamide, Tolazanide, Chloropropramide, glyburide, glopizide and metformin.

10. A method of screening a composition for the ability to treat non-insulin dependent diabetes mellitus comprising determining if the composition decreases hepatic expression of the alpha subunit of a $G_s$ protein in a liver cell plasma membrane, thereby inhibiting stimulation of cyclic adenosine monophosphate by glucagon, whereby a composition which decreases the hepatic expression of the alpha subunit of the $G_s$ protein in the liver cell plasma membrane and inhibits the stimulation of cyclic adenosine monophosphate by glucagon, is identified as a composition with the ability to treat non-insulin dependent diabetes mellitus.

11. The method of claim 2 wherein the pancreatic polypeptide is administered in an effective dose ranging between 2 and 500 µg/kg body weight/day.

12. The method of claim 2, wherein the pancreatic polypeptide is administered in an effective dose ranging between 4 and 100 µg/kg body weight/day.

13. The method of claim 6, wherein the carboxyl terminal fragment of pancreatic polypeptide having the amino acid sequence of SEQ ID NO:2 is administered in an effective dose ranging between 20 and 5,000 µg/kg body weight/day.

14. A method for treating non-insulin dependent diabetes mellitus in a patient diagnosed with non-insulin dependent diabetes mellitus by administering to the patient a composition comprising a compound selected from the group consisting of pancreatic polypeptide and the carboxyl terminal fragment of pancreatic polypeptide having the amino acid sequence of SEQ ID NO:2, in a pharmaceutically acceptable carrier, that inhibits beta cell and pancreatic islet hypertrophy in a patient by binding the vagal nuclear complex, thereby inhibiting secretion of digestive enzymes by the exocrine pancreas in the patient, whereby the inhibition of beta cell and pancreatic islet hypertrophy treats the non-insulin dependent diabetes mellitus.

15. The method of claim 14, wherein the compound is pancreatic polypeptide.

16. The method of claim 14, wherein the compound is the carboxyl terminal fragment of pancreatic polypeptide having the amino acid sequence of SEQ ID NO:2.

17. A method of screening a composition for the ability to treat non-insulin dependent diabetes mellitus comprising determining if the composition binds the vagal nuclear complex and inhibits secretion of digestive enzymes by the exocrine pancreas, thereby inhibiting beta cell and pancreatic islet hypertrophy, whereby a composition which binds the vagal nuclear complex and inhibits secretion of digestive enzymes by the exocrine pancreas, thereby inhibiting beta cell and pancreatic islet hypertrophy, is identified as a composition with the ability to treat non-insulin dependent diabetes mellitus.

18. A method for treating non-insulin dependent diabetes mellitus in a patient diagnosed with non-insulin dependent diabetes mellitus by administering to the patient a composition comprising a compound selected from the group consisting of pancreatic polypeptide and the carboxyl terminal fragment of pancreatic polypeptide having the amino acid sequence of SEQ ID NO:2, in a pharmaceutically acceptable carrier, that enhances insulin sensitivity and reverses the effects of neuropeptide Y in the patient by binding the arcuate nucleus in the hypothalamus, thereby potentiating the effect of leptin in reducing neuropeptide Y synthesis, whereby the enhancement of insulin sensitivity and reversal of the effects of neuropeptide Y treat the non-insulin dependent diabetes mellitus.

19. The method of claim 18, wherein the compound is pancreatic polypeptide.

20. The method of claim 18, wherein the compound is the carboxyl terminal fragment of pancreatic polypeptide having the amino acid sequence of SEQ ID NO:2.

21. A method of screening a composition for the ability to treat non-insulin dependent diabetes mellitus comprising determining if the composition binds the arcuate nucleus in the hypothalamus and potentiates the effect of leptin in reducing neuropeptide Y synthesis, thereby enhancing insulin sensitivity and reversing the effects of neuropeptide Y, whereby a composition which enhances insulin sensitivity and reverses the effects of neuropeptide Y is identified as a composition with the ability to treat non-insulin dependent diabetes mellitus.

22. A therapeutic composition consisting essentially of pancreatic polypeptide and insulin.

23. A therapeutic composition consisting essentially of pancreatic polypeptide and an oral hypoglycemic agent.

24. The therapeutic composition of claim 23, wherein the oral hypoglycemic agent is selected from the group consisting of Tobutanine, Acetohexamide, Tolazanide, Chloropropramide, glyburide, glopizide and metformin.

25. A kit comprising the therapeutic composition of claim 22 in a pharmaceutically acceptable carrier.

26. A kit comprising the therapeutic composition of claim 23 in a pharmaceutically acceptable carrier.

* * * * *